US011247954B2

(12) United States Patent
Oelmann et al.

(10) Patent No.: US 11,247,954 B2
(45) Date of Patent: *Feb. 15, 2022

(54) PROCESS FOR THE MULTISTAGE PRODUCTION OF METHANOL

(71) Applicant: L'Air Liquide, Société Anonyme pour l'Etude et l'Exploitation des Procédés Georges Claude, Paris (FR)

(72) Inventors: Tobias Oelmann, Bad Vilbel (DE); Veronika Gronemann, Karben (DE); Heiko Hofmann, Langen (DE); Timm Schuhmann, Bensheim (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/072,299

(22) Filed: Oct. 16, 2020

(65) Prior Publication Data
US 2021/0114956 A1   Apr. 22, 2021

(30) Foreign Application Priority Data

Oct. 16, 2019   (EP) .................................... 19020578

(51) Int. Cl.
*C07C 29/151* (2006.01)
*B01J 19/00* (2006.01)
(Continued)

(52) U.S. Cl.
CPC ....... *C07C 29/1516* (2013.01); *B01J 19/0013* (2013.01); *B01J 19/24* (2013.01);
(Continued)

(58) Field of Classification Search
CPC ... C07C 29/1516; C07C 31/04; C07C 29/152; C07C 29/154; B01J 19/0013; B01J 35/026; B01J 19/24
See application file for complete search history.

(56) References Cited

U.S. PATENT DOCUMENTS

| 4,326,041 A | 4/1982 | Bähnisch |
| 5,827,901 A | 10/1998 | König et al. |

(Continued)

FOREIGN PATENT DOCUMENTS

| DE | 29 34 332 | 3/1981 |
| DE | 10 2010 008 857 | 8/2011 |

(Continued)

OTHER PUBLICATIONS

Ullmann's Encyclopedia of Industrial Chemistry, $6^{th}$ Ed. 1998 electronic release, Methanol, 5.2 Synthesis, 620-621.

(Continued)

*Primary Examiner* — Jafar F Parsa
(74) *Attorney, Agent, or Firm* — Elwood L. Haynes

(57) ABSTRACT

Proposed is a process for producing methanol from synthesis gas by means of multi-stage, for example 2-stage, heterogeneously catalyzed methanol synthesis, wherein the product stream of a synthesis stage is applied to the downstream synthesis stage as a feed stream or after removal of a purge stream recycled to the first synthesis stage as a recycle stream. According to the invention a substream is removed from the synthesis gas fresh gas and introduced into the second methanol synthesis reactor as a bypass stream.

8 Claims, 2 Drawing Sheets

(51) Int. Cl.
    *B01J 19/24*     (2006.01)
    *B01J 35/02*     (2006.01)
    *C07C 29/152*     (2006.01)
    *C07C 29/154*     (2006.01)
    *B01J 23/72*     (2006.01)
    *C07C 31/04*     (2006.01)

(52) U.S. Cl.
    CPC ........... B01J 35/026 (2013.01); C07C 29/152 (2013.01); C07C 29/154 (2013.01); *B01J 23/72* (2013.01); *C07C 31/04* (2013.01)

(56) References Cited

U.S. PATENT DOCUMENTS

2007/0225385 A1*   9/2007   Early .................. C07C 29/1516
                                                518/705
2011/0178187 A1   7/2011   Kopetsch
2012/0322651 A1   12/2012   Schlichting et al.

FOREIGN PATENT DOCUMENTS

| DE | 10 2008 049 622 B4 | 10/2012 |
| EP | 0 790 226 | 6/1997 |
| EP | 1 016 643 | 7/2000 |
| WO | WO 2006 018610 | 2/2006 |
| WO | WO 2017 121981 | 7/2017 |

OTHER PUBLICATIONS

European Search Report for corresponding EP 19020578, Apr. 1, 2020.

\* cited by examiner

# PROCESS FOR THE MULTISTAGE PRODUCTION OF METHANOL

CROSS REFERENCE TO RELATED APPLICATIONS

This application claims the benefit of priority under 35 U.S.C. § 119 (a) and (b) to European Patent Application No. 19020578.1, filed Oct. 16, 2019, the entire contents of which are incorporated herein by reference.

BACKGROUND

Field of the Invention

The invention relates to a process for producing methanol by heterogeneously catalyzed conversion of synthesis gas comprising hydrogen and carbon oxides over solid, granular catalysts for methanol synthesis arranged in a plurality of serially arranged fixed-bed reactors. The invention further relates to a plant for performing such a production process.

Prior Art

Processes for industrial production of methanol by heterogeneously catalyzed conversion of synthesis gas, i.e. mixtures of hydrogen and carbon oxides, have long been known in the art. Ullmann's Encyclopedia of Industrial Chemistry, Sixth Edition, 1998 Electronic Release, chapter "Methanol", subchapter 5.2 "Synthesis" describes various basic processes for producing methanol by catalytic conversion of synthesis gas comprising hydrogen and carbon oxides in which such reactors are employed.

A modern two-stage process for producing methanol is disclosed in European patent specification EP 0 790 226 B1 for example. The methanol is produced in a circular process wherein a mixture of fresh and partly reacted synthesis gas is supplied initially to a water-cooled reactor (WCR) and then to a gas-cooled reactor (GCR), in each of which the synthesis gas is converted over a copper-based fixed-bed catalyst to afford methanol. The methanol produced in the process is separated from the synthesis gas to be recycled which is then passed through the gas-cooled reactor in countercurrent as coolant and preheated to a temperature of 220° C. to 280° C. before it is introduced into the first synthesis reactor. A portion of the synthesis gas to be recycled is removed from the process as a purge stream to prevent inert components from accumulating in the synthesis circuit. This measure is also taught in German laid-open specification DE 2934332 A1 and European patent application EP 1016643 A1.

The water-cooled reactor stage typically achieves the main conversion of the synthesis gas ($CO$, $CO_2$, $H_2$) and removes the largest portion of the reaction heat while the gas-cooled stage converts a nevertheless considerable portion of the synthesis gas under milder conditions.

The water-cooled reactor (WCR) is typically a shell-and-tube reactor comprising corresponding tube plates, wherein the catalyst is filled into the tubes while cooling is effected by means of boiling water/steam generation on the shell side around the tubes. In the gas-cooled reactor (GCR) cooling is effected with the input gas which is passed through the tubes and is heated on the way to the first reaction stage (WCR) while the catalyst is filled around the tubes and the reaction takes place on the shell side of the GCR. In terms of their nominal width the reaction stages are connected with large or very large pipelines; depending on plant capacity pipe diameters of up to 1 m are possible. This is attributable above all to the large gas amounts which are recycled to the second stage (recycle gas) and admixed with the fresh gas or make-up gas, i.e. fresh synthesis gas, from gas production. After preheating in the GCR the resulting gas mixture of recycle gas and fresh gas is supplied to the first reaction stage (WCR). The recycle gas amount is typically markedly greater than the fresh gas amount and depends on the achieved conversion in the reactor section. The recycle ratio RR (RR=R/F) of recycle gas amount (R) to fresh gas amount (F) is often above 2 and in many cases even above 3.5. The lower the per-pass conversion of synthesis gas by the reactor section, the higher the recycle ratio RR required to achieve sufficient yield. This leads to a corresponding increase in the circulating gas quantity which increases the space velocity of the reactors and requires greater nominal pipe widths of the connecting pipelines and also results in an increased demand for compression energy (higher flow rate and pressure drop).

It is customary for both synthesis reactors to use the same copper-based methanol synthesis catalysts which are employed as solid, granular catalysts in fixed-bed reactors. In the described two-stage WCR-GCR process the water-cooled reactor is typically operated with a higher synthesis gas entry temperature than a water-cooled reactor in a single-stage process for methanol synthesis in order to allow provision of higher-pressure steam. This reactor is further provided with synthesis gas that is not yet fully reacted. The high exothermicity of the methanol synthesis therefore requires very good temperature control of the reactor to avoid overheating of the catalyst which contributes substantially to premature deactivation thereof. German laid-open specification DE 102010008857 A1 therefore proposes using catalysts having different activities in the two synthesis reactors, wherein the reactor having the more drastic reaction conditions is to employ a catalyst of lower activity having a lower deactivation rate and thus higher long-term stability.

However, the disadvantage of this process is that catalysts of different activity must be provided, thus complicating the logistics required for plant operation. In addition, there is also a need for improved control of the individual synthesis reactors, especially in respect of the temperatures prevailing therein. Excessive local temperatures, so-called "hotspots", are a substantial factor for premature deactivation of the employed catalysts.

SUMMARY

It is accordingly an object of the present invention to specify a process and plant which does not exhibit the described disadvantages of the prior art and which especially makes it possible in a multistage process/a multistage plant for methanol synthesis having a plurality of serially connected synthesis reactors to achieve a more uniform space velocity of the catalysts arranged in the individual reactors and further to achieve improved temperature control therein.

This object is achieved by a process having the features of claim 1. Further embodiments of the invention are apparent from the subsidiary claims of the respective category.

Process According to the Invention

Process for producing methanol by converting a synthesis gas input stream containing hydrogen and carbon oxides, comprising the following process steps:

(a) providing the synthesis gas input stream containing hydrogen and carbon oxides, separating the synthesis gas input stream into a fresh gas bypass stream and into a fresh gas feed stream, (b) combining and mixing the fresh gas feed stream with a recycle stream containing hydrogen and carbon oxides to afford a first reactor feed stream, (c) introducing the first reactor feed stream into a first methanol synthesis reactor containing at least one catalyst zone comprising a solid, granular catalyst active for methanol synthesis, at least partially converting the first reactor feed stream in the first methanol synthesis reactor under methanol synthesis conditions, (d) discharging a first reactor product stream containing methanol and water from the first methanol synthesis reactor, (e) introducing the first reactor product stream as first part of a second reactor feed stream into a second methanol synthesis reactor containing at least one catalyst zone comprising a solid, granular catalyst active for methanol synthesis, at least partially converting the first residual gas stream in the second methanol synthesis reactor under methanol synthesis conditions, (f) discharging a second reactor product stream containing methanol and water from the second methanol synthesis reactor, cooling the second reactor product stream below its dew point and supplying the cooled second reactor product stream to a phase separation apparatus, (g) separating the cooled second reactor product stream in the phase separation apparatus into a liquid product stream and a gas product stream containing unconverted synthesis gas constituents, (h) separating the gas product stream into a purge stream which is discharged from the process and into the recycle stream which is recycled to step (b), (i) discharging the liquid product stream from the process as a crude methanol product stream, characterized in that (j) the fresh gas bypass stream is introduced as second part of the second reactor feed stream into the second methanol synthesis reactor.

Plant According to the Invention

Plant for producing methanol by converting a synthesis gas input stream containing hydrogen and carbon oxides, comprising the following assemblies and constituents in fluid connection with one another:

(a) means for providing the synthesis gas input stream containing hydrogen and carbon oxides, means for separating the synthesis gas input stream into a fresh gas bypass stream and into a fresh gas feed stream, (b) means for combining and mixing the fresh gas feed stream with a recycle stream containing hydrogen and carbon oxides to afford a first reactor feed stream, (c) a first methanol synthesis reactor containing at least one catalyst zone comprising a solid, granular catalyst active for methanol synthesis, means for introducing the first reactor feed stream into the first methanol synthesis reactor, (d) means for discharging a first reactor product stream containing methanol and water from the first methanol synthesis reactor, (e) a second methanol synthesis reactor containing at least one catalyst zone comprising a solid, granular catalyst active for methanol synthesis, means for introducing the first reactor product stream as first part of a second reactor feed stream into the second methanol synthesis reactor, (f) means for discharging a second reactor product stream containing methanol and water from the second methanol synthesis reactor, a phase separation apparatus, means for cooling the second reactor product stream below its dew point and means for supplying the cooled second reactor product stream to the phase separation apparatus, (g) means for separating the cooled second reactor product stream in the phase separation apparatus into a liquid product stream and a gas product stream containing unconverted synthesis gas constituents, means for discharging the liquid product stream, means for discharging the gas product stream, (h) means for separating the gas product stream into a purge stream and a recycle stream, means for discharging the purge stream from the process, means for recycling the recycle stream to assembly (b), (i) means for discharging the liquid product stream from the process as a crude methanol product stream, characterized in that (j) it comprises means that make it possible to introduce the fresh gas bypass stream as second part of the second reactor feed stream into the second methanol synthesis reactor.

Fluid connection between two regions of the reactor according to the invention is to be understood as meaning any type of connection whatsoever which makes it possible that a fluid, for example the input gas stream or the synthesis gas product stream, can flow from the one to the other of the two regions, neglecting any interposed regions or components.

Methanol synthesis conditions are to be understood as meaning the process conditions known per se to a person skilled in the art, in particular of temperature, pressure and residence time, as recited by way of example above and discussed in detail in the relevant literature and under which at least partial conversion but preferably industrially relevant conversions of the reactants $CO/CO_2$ and hydrogen into the product methanol is effected. Accordingly, a catalyst active for methanol synthesis is to be understood as meaning a catalyst which brings about precisely such conversions under methanol synthesis conditions.

A means is to be understood as meaning something that enables or is helpful in the achievement of a goal. In particular, means for performing a particular process step are to be understood as including all physical articles that would be considered by a person skilled in the art in order to be able to perform this process step. For example, a person skilled in the art will consider means of introducing or discharging a material stream to include all transporting and conveying apparatuses, i.e. for example pipelines, pumps, compressors, valves and the corresponding openings in container walls which seem necessary or sensible to said skilled person for performance of this process step on the basis of his knowledge of the art.

Catalytic activity, especially in connection with different catalytic activities when comparing two different catalysts, is to be understood as meaning the achieved degree of conversion per unit length of the catalyst bed of reactants to products. Activity is influenced by the chemical composition, doping, poisoning, available surface area etc. of the catalyst material but also by the geometry of the catalyst particles and textural parameters of the catalyst bed, for example its porosity or packing density. Due to the exothermicity of the reactions considered a high catalytic activity correlates with a high evolution of heat per unit length of the catalyst bed. The quantity flow of liquid products collected by condensation constitutes a further measure of catalyst activity under specified methanol synthesis conditions since the reaction products of the methanol synthesis reaction according to the conversion equations $$CO(g) + 2H_2(g) = CH_3OH(l)$$

$$CO_2(g) + 3H_2(g) = CH_3OH(l) + H_2O(l)$$

are liquid under ambient conditions. Accordingly, the parameter "activity loss" describes the decrease over time of catalyst activity and degree of reactant conversion/methanol yield.

A first/second methanol synthesis reactor is not necessarily to be understood as meaning individual reactors but rather this term may also comprise respective groups of individual reactors which in turn may also contain one or more catalyst zones, i.e. regions filled with solid, granular methanol synthesis catalyst. The terms "first" and "second" methanol synthesis reactor are thus merely to be understood as indicating the traversal sequence of the reactors considered. The first/second methanol synthesis reactor need not necessarily follow one another in direct succession but rather may have further methanol synthesis reactors not considered in detail here arranged between them. It is characteristic of the second methanol synthesis reactor that according to the invention the fresh gas bypass stream is introduced thereinto.

A catalyst cycle is to be understood as meaning the operating duration of one batch of a methanol synthesis catalyst commencing with the bringing online of the methanol synthesis operation in the methanol synthesis reactor filled with the batch of fresh or regenerated methanol synthesis catalyst and terminating with the taking offline of the methanol synthesis operation in the same methanol synthesis reactor for purposes of catalyst replacement or performing catalyst regeneration.

The present invention is based on the finding that the activity loss of a methanol synthesis catalyst as a result of catalyst deactivation is caused by various main criteria which include in particular high temperatures, production quantity per unit time and accumulation of catalyst poisons and loss of active centers. In multistage processes/plants having serially arranged reactor systems the catalysts in the individual synthesis reactors are deactivated at varying rates. Thus, for example the first reactor in the flow direction has a higher space velocity since it is subjected to more reactive synthesis gas containing a higher concentration of the reactant components. This results in higher maximum temperatures in the catalyst bed and an initially higher production rate which, however, then falls relatively rapidly compared to downstream reactors. When the specified total production capacity of the plant is no longer achieved despite exhausting possible operating parameter adjustments, the catalysts in the synthesis reactors are replaced. The catalyst in the first reactor in the flow direction normally shows more severe deactivation than the catalyst in the one or more downstream reactors. Separate replacement of only the catalyst in the first reactor is theoretically possible but logistically difficult and is therefore avoided. In any case, even replacement of the catalyst in only one synthesis reactor requires shutdown of the entire synthesis plant. It is therefore unattractive to replace the catalyst in only one synthesis reactor since otherwise further shutdowns for replacement of the initially less deactivated catalysts in subsequent reactors must be expected.

The inventive synthesis gas introduction ahead of a downstream, for example second, synthesis reactor ensures that all reaction zones have a more uniform space velocity, thus resulting in a more uniform and thus more efficient utilization of the catalyst. This makes it possible to reduce the recycle ratio RR and the reactor volume and further results in extended catalyst lifetime, higher production capacities and accordingly in cost reductions for the overall process. This is achieved by introducing the reactive synthesis gas ahead of a downstream, for example second, methanol synthesis reactor which is thus subjected from the outset to synthesis gas having a higher concentration of the reactant components. The first methanol synthesis reactor has a lower space velocity due to the dilution of the synthesis gas with recycle gas. This allows the catalyst in the downstream, for example second, methanol synthesis reactor to be better utilized and the synthesis performed more efficiently.

With increasing activity loss of the catalyst in the synthesis reactors the amount of fresh synthesis gas to a downstream, for example second, reactor may be reduced to increase the residence time of the synthesis gas in this synthesis reactor and thus compensate the methanol yield loss increasing over time. It has further been surprisingly found that the recycling ratio RR can be markedly reduced with the interconnection according to the invention. Depending on the intended production capacity and gas composition a reduction can be achieved of the recycle ratio RR from values customary according to the prior art of between 1.6 and 2.5 to values according to the invention of between 1.0 and 2.0 upon achieving the production capacity.

PREFERRED EMBODIMENTS OF THE INVENTION

A particular embodiment of the process according to the invention is characterized in that the fresh gas bypass stream is combined and mixed with the first reactor product stream to obtain the second reactor feed stream prior to introduction into the second methanol synthesis reactor. This ensures a uniform reactant concentration at the entrance of the second methanol synthesis reactor and avoids the formation of concentration streaks which can result in nonuniform reactor operation.

A further embodiment of the process according to the invention is characterized in that the quantity flow of the fresh gas bypass stream introduced into the second methanol synthesis reactor is altered on a continuous or stepwise basis over a catalyst cycle. This affords a further degree of freedom for ensuring uniform operation of the production plant and countering unwanted deviations from the target operating parameters, for example temperature spikes in the catalyst beds.

A further embodiment of the process according to the invention is characterized in that the quantity flow of the fresh gas bypass stream introduced into the second methanol synthesis reactor is reduced on a continuous or stepwise basis over a catalyst cycle. This embodiment comprises for example reducing the amount of fresh synthesis gas to the second synthesis reactor with increasing activity loss of the catalyst in the synthesis reactors to increase the residence time of the synthesis gas in this synthesis reactor and thus compensate the methanol yield loss increasing over time. The remaining fresh gas proportion not passed to the second synthesis reactor is additionally supplied to the first synthesis reactor so that the residence time of the synthesis gas falls in the first synthesis reactor but remains constant over the sum of both reactors.

A further embodiment of the process according to the invention is characterized in that over a catalyst cycle the quantity flow of the fresh gas bypass stream introduced into the second methanol synthesis reactor is reduced on a continuous or stepwise basis according to the activity loss of the catalyst in the first and/or second methanol synthesis reactor. This embodiment accordingly comprises reducing the amount of fresh synthesis gas to the second synthesis reactor with increasing activity loss of the catalyst in the synthesis reactors to increase the residence time of the synthesis gas in this synthesis reactor and thus compensate the methanol yield loss increasing over time. The remaining fresh gas proportion not passed to the second synthesis reactor is additionally supplied to the first synthesis reactor so that the residence time of the synthesis gas falls in the first synthesis reactor but remains constant over the sum of both reactors. In this embodiment a relatively large proportion of the fresh gas flows through both reactors so that despite the activity loss of the catalyst in the first and/or second methanol synthesis reactor the methanol yield increases again or is maintained.

One option for determining catalyst activity in the individual methanol synthesis reactors, for example in the first or second methanol synthesis reactor, is that of sampling the individual reactor product streams via sampling points attached to the reactor outlets and analysis of these samples in a manner known to those skilled in the art, thus allowing the synthesis gas conversion and the methanol yield in the individual reactors to be determined.

A further embodiment of the process according to the invention is characterized in that over a catalyst cycle the quantity flow of the fresh gas bypass stream introduced into the second methanol synthesis reactor is reduced from a starting value to an end value on a continuous or stepwise basis, wherein the starting value corresponds to at most 40% by volume of the synthesis gas input stream. Investigations have shown that this starting value makes it possible to achieve particularly good temperature control in both reactors and a particularly advantageous methanol yield.

A further embodiment of the process according to the invention is characterized in that the first methanol synthesis reactor is in the form of a water-cooled reactor (WCR) and the second methanol synthesis reactor is in the form of a water-cooled reactor (WCR) or a gas-cooled reactor (GCR), wherein the first reactor feed stream is passed as cooling gas through the second, gas-cooled methanol synthesis reactor and thus heated against the second reactor product stream in indirect heat exchange prior to introduction into the first, water-cooled methanol synthesis reactor. The gas-cooled reactor thus fulfils two functions, namely as a synthesis reactor and as a heat exchanger/feed preheater for the WCR. Good temperature control of the second reactor as is made possible by the fresh feed introduction according to the invention is therefore particularly important in the embodiment according to the WCR-GCR concept.

A further embodiment of the process according to the invention is characterized in that the second methanol synthesis reactor is in the form of a gas-cooled reactor (GCR), wherein the first reactor feed stream is passed through the second, gas-cooled methanol synthesis reactor in cocurrent with the second reactor product stream and thus heated against the second reactor product stream in indirect heat exchange. This embodiment offers advantages due to the improved cooling at the reaction gas inlet. Compared to the countercurrent mode, the cocurrent mode further increases the difference in temperature between the cooling tube wall and the dew point of the product mixture. This means that even when operating the water-cooled first reactor at low temperatures the risk of condensation is markedly reduced. A further result is a flatter temperature curve over the reactor length with lower peak temperatures. This is advantageous for the service life stability of the catalyst.

A particular embodiment of the plant according to the invention is characterized in that it further comprises means for combining and mixing the fresh gas bypass stream with the first reactor product stream. This ensures a uniform reactant concentration at the entrance of the first methanol synthesis reactor and avoids the formation of concentration streaks which can result in nonuniform reactor operation.

A further advantageous embodiment of the plant according to the invention is characterized in that the first methanol synthesis reactor is in the form of a water-cooled reactor (WCR) and the second methanol synthesis reactor is in the form of a water-cooled reactor (WCR) or a gas-cooled reactor (GCR), wherein said plant further comprises means that make it possible for the first reactor feed stream to be passed as cooling gas through the second, gas-cooled methanol synthesis reactor and thus heated against the second reactor product stream in indirect heat exchange prior to introduction into the first, water-cooled methanol synthesis reactor. The gas-cooled reactor thus fulfils two functions, namely as a synthesis reactor and as a heat exchanger/feed preheater for the WCR. Good temperature control of the second reactor as is made possible by the fresh feed introduction according to the invention is therefore particularly important in the embodiment according to the WCR-GCR concept.

A further aspect of the plant according to the invention is characterized in that the second methanol synthesis reactor is in the form of a gas-cooled reactor (GCR) and is further configured to make it possible for the first reactor feed stream to be passed through the second, gas-cooled methanol synthesis reactor in cocurrent with the second reactor product stream and thus heated against the second reactor product stream in indirect heat exchange. This embodiment offers advantages due to the improved cooling at the reaction gas inlet. Compared to the countercurrent mode, the cocurrent mode further increases the difference in temperature between the cooling tube wall and the dew point of the product mixture. This means that even when operating the water-cooled first reaction at low temperatures the risk of condensation is markedly reduced. A further result is a flatter temperature curve over the reactor length with lower peak temperatures. This is advantageous for the service life stability of the catalyst.

A further aspect of the plant according to the invention is characterized in that the second methanol synthesis reactor is in the form of a gas-cooled reactor (GCR) and comprises a reactor shell and in the interior thereof a multiplicity of tubes, wherein the solid, granular catalyst active for methanol synthesis is arranged either in the tubes or in the intermediate space between the inside of the reactor shell and the outside of the tubes and wherein the first reactor feed stream is passed as cooling gas through the respective other region not containing catalyst. It is particularly preferable when the catalyst is arranged in the intermediate space between the inside of the reactor shell and the outside of the tubes and the tubes are traversed by the first reactor feed stream as cooling gas.

BRIEF DESCRIPTION OF THE DRAWINGS

Developments, advantages and possible applications of the invention are also apparent from the following description of working examples and the drawings. All the features described and/or shown in images, alone or in any combination, form the invention, irrespective of the way in which they are combined in the claims or the dependency references therein.

DETAILED DESCRIPTION OF PREFERRED EMBODIMENTS

Figure 1:
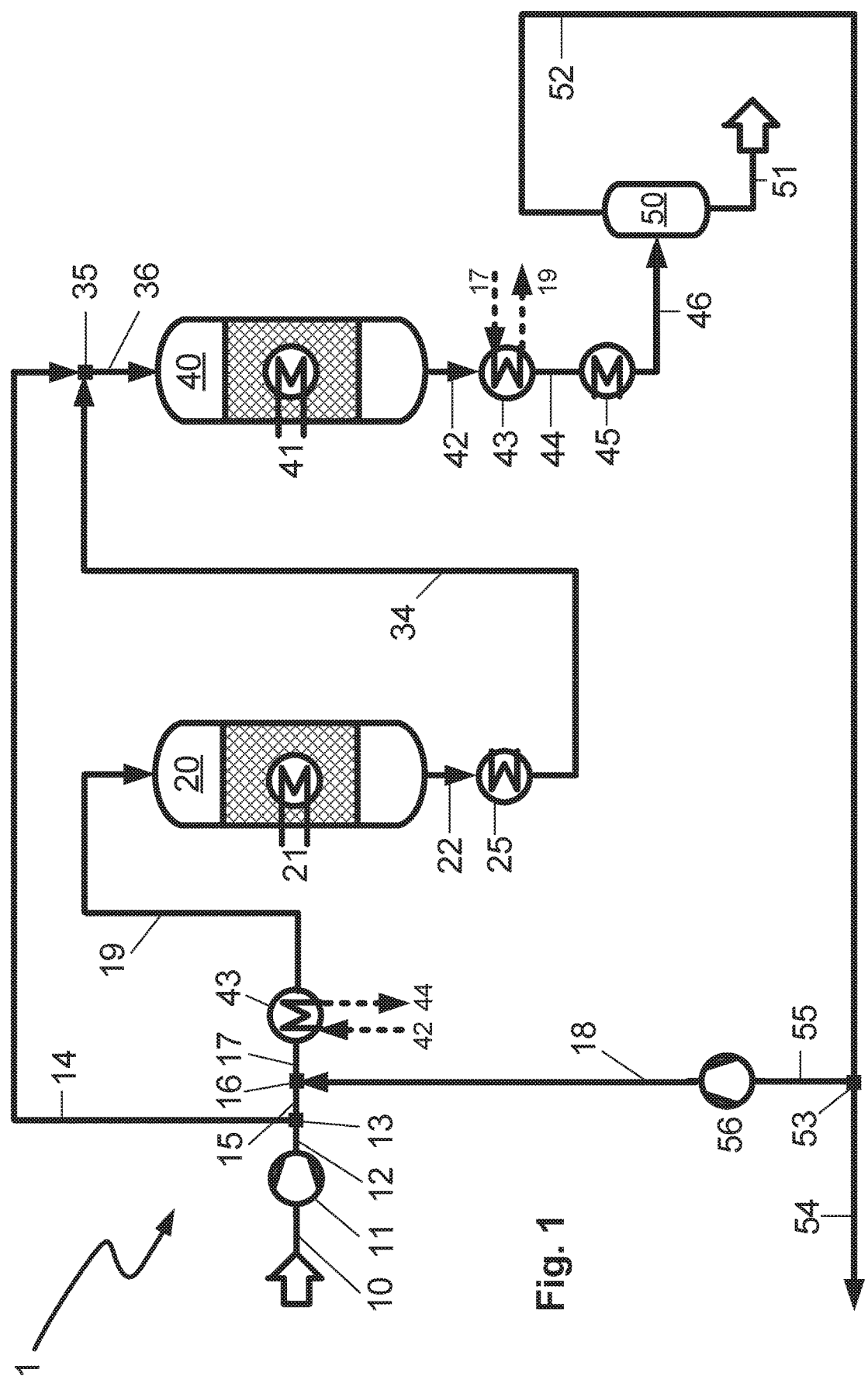
FIG. 1 is a schematic representation of the process/the plant according to a first embodiment of the invention comprising two water-cooled reactors.

In the first embodiment of a process 1/a plant 1 according to the invention shown in FIG. 1 which comprises two serially arranged, water-cooled synthesis reactors 20, 40, fresh synthesis gas (fresh gas, make-up gas) containing hydrogen, carbon monoxide and carbon dioxide from a synthesis gas production plant (not shown) is introduced via conduit 10, compressed to synthesis pressure using compressor 11 and passed via conduit 12 to a separation apparatus 13 which may be in the form of a pipe T-piece for example. A substream of the fresh gas is discharged from the separation apparatus via conduit 14 and passed as fresh gas bypass stream to the second synthesis reactor 40. A metering apparatus (not shown) may be arranged along the course of conduit 14 by means of which the quantity flow of the fresh gas bypass stream may be adjusted.

The remaining proportion of the fresh gas is passed via conduit 15 as fresh gas feed stream to the mixing apparatus 16 and therein combined with a recycle stream which is provided via conduit 18 and likewise introduced into the mixing apparatus 16. The mixing apparatus 16, as well as the mixing apparatuses recited hereinbelow, may be in the form of a pipe T-piece or a static mixer for example. The ratio of the quantity flows passed via conduits 18 (recycle stream) and 15 (fresh gas) to the mixing apparatus 16 corresponds to the recycle ratio RR.

The combining and mixing of the fresh gas feed stream with the recycle stream affords a first reactor feed stream which is passed via conduit 17 to heat exchanger 43 and therein heated to the reactor entry temperature in indirect heat exchange with the hot reactor product stream from the second synthesis reactor 40. Said stream is then introduced via conduit 19 into the first methanol synthesis reactor 20.

Partial conversion of the first reactor feed stream is carried out under methanol synthesis conditions in the first methanol synthesis reactor 20 which contains at least one catalyst zone comprising a solid, granular catalyst active for methanol synthesis. In the exemplary embodiment of FIG. 1 both synthesis reactors 20, 40 are water-cooled; the respective cooling apparatuses integrated into the reactors are indicated by reference numerals 21, 41.

A hot first reactor product stream is discharged from the first synthesis reactor 20 via conduit 22 and passed to an optional cooler 25. The optionally cooled first reactor product stream is subsequently passed as first part of a second reactor feed stream via conduit 34 to mixing apparatus 35.

Mixing apparatus 35 combines and mixes the heated first residual gas stream with the fresh gas bypass stream provided via conduit 14 as second part of the second reactor feed stream. Mixing apparatus 35 may also be in the form of a pipe T-piece or a static mixer for example. The thus obtained second reactor feed stream is then introduced via conduit 36 into the second methanol synthesis reactor 40 which likewise contains at least one catalyst zone comprising a solid, granular catalyst active for methanol synthesis. The second methanol synthesis reactor carries out the partial conversion of the second reactor feed stream under methanol synthesis conditions.

A hot second reactor product stream is discharged from the second methanol synthesis reactor 40 via conduit 42 and passed to heat exchanger 43 and then, via conduit 44, to cooler 45. Heat exchanger 43 carries out a first cooling of the hot second reactor product stream by indirect heat exchange with the first reactor feed stream provided via conduit 17. Cooler 45 may be operated for example as an air cooler or as a cooler operated with cooling water. The second reactor product stream cooled below its dew point is introduced via conduit 46 into a phase separation apparatus 50 and therein separated into a liquid product stream and into a gas product stream. The liquid product stream which contains substantially methanol and water is discharged from the process/ from the plant via conduit 51 and supplied to the crude methanol workup (not shown). The gas product stream containing as yet unconverted synthesis gas constituents is passed via conduit 52 to separation apparatus 53.

Separation apparatus 53 which may be in the form of a pipe T-piece for example carries out the separation of the gas product stream into a purge stream discharged from the process/the plant via conduit 54 and into a recycle stream passed via conduit 55 to compressor 56. The discharging of the purge stream via conduit 54 serves to prevent accumulation of inert components such as for example argon or methane within the synthesis circuit. To adjust the purge stream quantity flow a metering valve (not shown) may be provided in the flow path of the conduit 54.

The compressed recycle stream is discharged from compressor 56 via conduit 18 and introduced into mixing apparatus 16.

Figure 2:
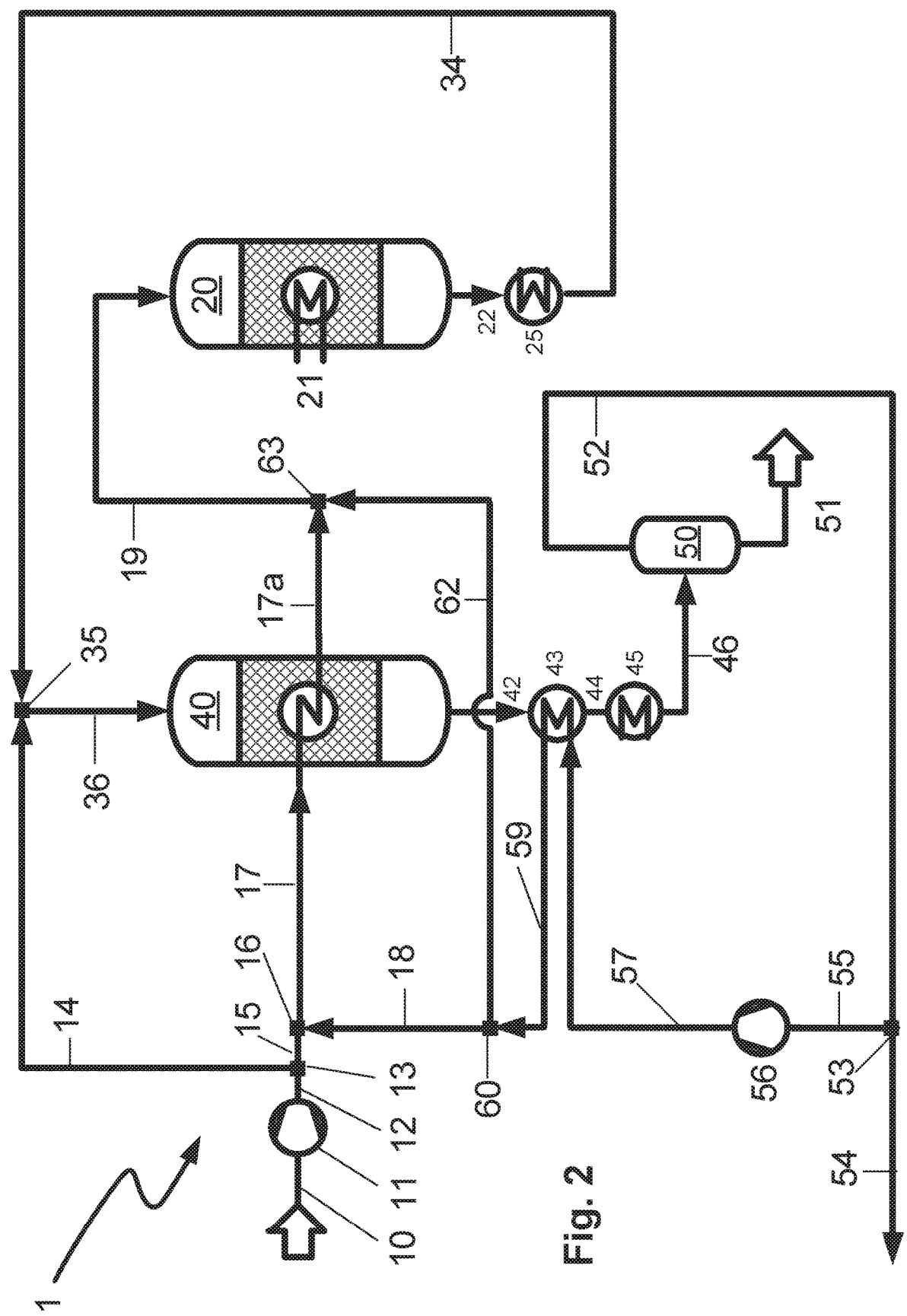
FIG. 2 is a schematic representation of the process/the plant according to a second embodiment of the invention comprising a water-cooled reactor as the first reactor and a gas-cooled reactor as the second reactor.

In the second embodiment of the invention shown in FIG. 2 the process 1/the plant 1 comprises a water-cooled synthesis reactor 20 (WCR) and a gas-cooled synthesis reactor 40 (GCR). Unless otherwise specifically stated, drawing elements labelled with identical reference numerals correspond in function and constitution to those elucidated in connection with FIG. 1.

Compared to the first embodiment the embodiment of the invention shown in FIG. 2 has the following differences:

The first reactor feed stream is initially passed via conduit 17 to the gas-cooled reactor 40 (GCR), the second methanol synthesis reactor, therein passes through the integrated heat exchanger apparatus (indicated pictorially by the heat exchanger shown in the reactor) and is therein heated in indirect heat exchange with the hot reactor product gases. The first reactor feed stream simultaneously thus serves as the cooling gas stream in reactor 40. The heat exchanger 43 shown in FIG. 1 may normally be omitted and is therefore not shown pictorially in FIG. 2 but may optionally be provided as a backup or to realize particular operating conditions, for example for bringing the plant online. The heated first reactor feed stream is then passed via conduit 17a, mixing apparatus 63 and conduit 19 to the water-cooled reactor 20 (WCR) as the first methanol synthesis reactor and applied thereto. Via conduit 62 a substream of the recycle stream diverted using separation apparatus 60 may also be admixed with the first reactor feed stream for temperature adjustment using mixing apparatus 63. Adjustment of this substream quantity flow is effected for example with a metering apparatus (not shown) integrated into the conduit 62.

In contrast to FIG. 1, the cooling of the hot second reactor product stream discharged from the second methanol synthesis reactor 40 via conduit 42 in heat exchanger 43 is effected using the recycle stream provided in conduit 57 as cooling gas. The heated recycle stream is discharged from the heat exchanger 43 via conduit 59 and recycled to the first methanol synthesis reactor 20 via separation apparatus 60, conduit 18, mixing apparatus 16, conduit 17, 17a, mixing apparatus 63 and conduit 19.

LIST OF REFERENCE NUMERALS

1 Process, Plant
10 Conduit
11 Compressor
12 Conduit
13 Separation apparatus
14 Conduit
15 Conduit
16 Mixing apparatus
17 Conduit
18 Conduit
19 Conduit
20 First methanol synthesis reactor
21 Cooling apparatus
22 Conduit
25 Cooler
34 Conduit
35 Mixing apparatus
36 Conduit
40 Second methanol synthesis reactor
41 Cooling apparatus
42 Conduit
43 Heat exchanger
44 Conduit
45 Cooler
46 Conduit
50 Phase separation apparatus
51 Conduit
52 Conduit
53 Separation apparatus
54 Conduit
55 Conduit
56 Compressor
57 Conduit
59 Conduit
60 Separation apparatus
62 Conduit
63 Mixing apparatus It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing methanol by converting a synthesis gas input stream containing hydrogen and carbon oxides, comprising:
   (a) providing the synthesis gas input stream containing hydrogen and carbon oxides, separating the synthesis gas input stream into a fresh gas bypass stream and into a fresh gas feed stream,
   (b) combining and mixing the fresh gas feed stream with a recycle stream containing hydrogen and carbon oxides to afford a first reactor feed stream,
   (c) introducing the first reactor feed stream into a first methanol synthesis reactor containing at least one catalyst zone comprising a solid, granular catalyst active for methanol synthesis, at least partially converting the first reactor feed stream in the first methanol synthesis reactor under methanol synthesis conditions,
   (d) discharging a first reactor product stream containing methanol and water from the first methanol synthesis reactor,
   (e) introducing the first reactor product stream as first part of a second reactor feed stream into a second methanol synthesis reactor containing at least one catalyst zone comprising a solid, granular catalyst active for methanol synthesis, at least partially converting the first residual gas stream in the second methanol synthesis reactor under methanol synthesis conditions,
   (f) discharging a second reactor product stream containing methanol and water from the second methanol synthesis reactor, cooling the second reactor product stream below its dew point and supplying the cooled second reactor product stream to a phase separation apparatus,
   (g) separating the cooled second reactor product stream in the phase separation apparatus into a liquid product stream and a gas product stream containing unconverted synthesis gas constituents,
   (h) separating the gas product stream into a purge stream which is discharged from the process and into the recycle stream which is recycled to step (b),
   (i) discharging the liquid product stream from the process as a crude methanol product stream, wherein,
   (j) the fresh gas bypass stream is introduced as second part of the second reactor feed stream into the second methanol synthesis reactor.

2. The process according to claim 1, wherein the fresh gas bypass stream is combined and mixed with the first reactor product stream to obtain the second reactor feed stream prior to introduction into the second methanol synthesis reactor.

3. The process according to claim 1, wherein the quantity flow of the fresh gas bypass stream introduced into the second methanol synthesis reactor is altered on a continuous or stepwise basis over a catalyst cycle.

4. The process according to claim 3, wherein the quantity flow of the fresh gas bypass stream introduced into the second methanol synthesis reactor is reduced on a continuous or stepwise basis over a catalyst cycle.

5. The process according to claim 4, wherein, over a catalyst cycle the quantity flow of the fresh gas bypass stream introduced into the second methanol synthesis reactor is reduced on a continuous or stepwise basis according to the activity loss of the catalyst in the first and/or second methanol synthesis reactor.

6. The process according to claim 4, wherein, over a catalyst cycle the quantity flow of the fresh gas bypass stream introduced into the second methanol synthesis reactor is reduced from a starting value to an end value on a continuous or stepwise basis, wherein the starting value corresponds to at most 40% by volume of the synthesis gas input stream.

7. The process according to claim 1, wherein first methanol synthesis reactor is in the form of a water-cooled reactor (WCR) and the second methanol synthesis reactor is in the form of a water-cooled reactor (WCR) or a gas-cooled reactor (GCR), wherein the first reactor feed stream is passed as cooling gas through the second, gas-cooled methanol synthesis reactor and thus heated against the second reactor product stream in indirect heat exchange prior to introduction into the first, water-cooled methanol synthesis reactor.

8. The process according to claim 7, wherein the second methanol synthesis reactor is in the form of a gas-cooled reactor (GCR), wherein the first reactor feed stream is passed through the second, gas-cooled methanol synthesis reactor in cocurrent with the second reactor product stream and thus heated against the second reactor product stream in indirect heat exchange.

\* \* \* \* \*